(12) United States Patent
Niestroj et al.

(10) Patent No.: US 7,279,550 B2
(45) Date of Patent: Oct. 9, 2007

(54) IRREVERSIBLE CYSTEINE PROTEASE INHIBITORS OF LEGUMAIN

(75) Inventors: André Niestroj, Sennewitz (DE); Ulrich Heiser, Halle (Saale) (DE); Bernd Gerhartz, Lörrach (DE); Matthias Hoffmann, Wengelsdorf (DE); Hans-Ulrich Demuth, Halle (Saale) (DE)

(73) Assignee: Probiodrug AG, Halle (Saale) (DE)

( * ) Notice: Subject to any disclaimer, the term of this patent is extended or adjusted under 35 U.S.C. 154(b) by 387 days.

(21) Appl. No.: 10/485,723

(22) PCT Filed: Jul. 23, 2002

(86) PCT No.: PCT/EP02/08202

§ 371 (c)(1),
(2), (4) Date: Aug. 10, 2004

(87) PCT Pub. No.: WO03/016335

PCT Pub. Date: Feb. 27, 2003

(65) Prior Publication Data

US 2006/0178315 A1    Aug. 10, 2006

Related U.S. Application Data

(60) Provisional application No. 60/311,790, filed on Aug. 13, 2001.

(51) Int. Cl.
*C07K 5/023* (2006.01)
*C07F 9/28* (2006.01)
*C07C 229/26* (2006.01)

(52) U.S. Cl. .................... 530/331; 558/166; 560/155; 562/553

(58) Field of Classification Search .................... None
See application file for complete search history.

(56) References Cited

FOREIGN PATENT DOCUMENTS

EP    0 995 756 A2    4/2000
WO    WO95/23222    8/1995
WO    WO99/48910    9/1999

OTHER PUBLICATIONS

Demuth, et al.; "Molecular drug research: A survey of the mechanism-oriented serine protease inhibitors"; *Pharmazie*; (1989) 44(1), 1-11 (including abstract in English).
Dando, et al.; "Pig Kidney Legumain: an asparaginyl endopeptidase with restricted specificity"; *Biochem. J.*; (1999) 339, 743-749.
Ackermann, E. et al.; "Untersuchungen zur zentralnervösen Wirkung der Hydrazinoessigsäure and Ihrer Derivate"; *ACTA Biologica et Medica Germanica*; (1964) 12, 322-341 (including summary in English).
Gante, J; "Azapeptides"; *Synthesis*; (1989) 405-413.
Manoury, et al.; "An asparaginyl endopeptidase process a microbial antigen for class II MHC presentation"; *Nature*; (1998) 396, 695-699.
International Search Report dated Feb. 26, 2003.

*Primary Examiner*—Thurman K. Page
*Assistant Examiner*—Yevgeny Valenrod
(74) *Attorney, Agent, or Firm*—Sonnenschein Nath & Rosenthal LLP

(57) ABSTRACT

Presented are compounds represented by the following general formulas (I) and (II), for inhibiting cysteine protease legumain for modulating associated disease states in subjects

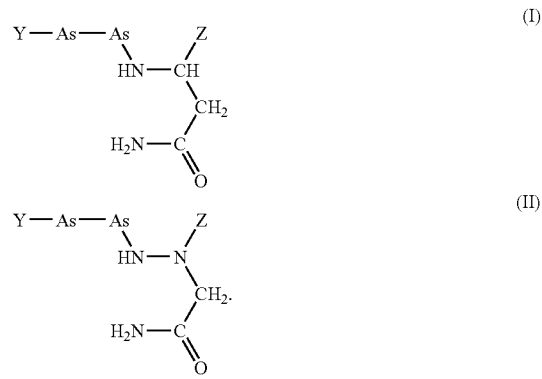

7 Claims, No Drawings

IRREVERSIBLE CYSTEINE PROTEASE INHIBITORS OF LEGUMAIN

FIELD OF THE INVENTION

The present invention relates to inhibitors of cysteine proteases, especially to inhibitors of the cysteine protease legumain. This invention relates further to pharmaceutical compositions containing one or more inhibitors of the legumain activity. The pharmaceutical compositions, comprising one or more legumain inhibitors according to the present invention are useful for the treatment of legumain mediated diseases in a patient or subject, such as immune or autoimmune diseases.

BACKGROUND OF INVENTION

Legumain was discovered in 1993 in plants, where the enzyme is present in legumes and in seeds of other plants. Then legumain was cloned, isolated and characterized from different species, e.g. from mouse, and from pig kidney. Human legumain was characterized after over-expression in a murine cell line.

The catalytic dyad is found in the motif His-Gly-spacer-Ala-Cys, and was confirmed by si-directed mutagenesis. Due to the presence of the same motif in caspases, clostripain, gingipain and separase these proteases where classified as Clan CD. Legumain is inhibited by iodoacetamid, maleimides, and ovocystatin, but is unaffected by E64.

Mammalian legumain is a lysosomal enzyme being highly specific for post-asparagine cleavage. It has been shown that the cleavage is inhibited by the glycosylation of the P1-asparagine residue. Furthermore, it is involved in the processing of antigens for the class II MHC presentation.

Different isoforms of legumain were purified from a plant source (seeds of kidney bean, *Phaseolus vulgaris*) and a mammal (kidney of pig, *Sus scropha*).

Autoimmune Reactions

Sometimes the immune system malfunctions, misinterprets the body's tissues as foreign, and attacks them, resulting in an autoimmune reaction. Autoimmune reactions can be triggered in several ways:

A substance in the body that is normally strictly contained in a specific area (and thus is hidden from the immune system) is released into the general circulation. For example, the fluid in the eyeball is normally contained within the eyeball's chambers. If a blow to the eye releases this fluid into the bloodstream, the immune system may react against it. A normal body substance is altered. For example, viruses, drugs, sunlight, or radiation may change a protein's structure in a way that makes it seem foreign. The immune system responds to a foreign substance that is similar in appearance to a natural body substance and inadvertently targets the body substance as well as the foreign substance. Something malfunctions in the cells that control antibody production. For example, cancerous B lymphocytes may produce abnormal antibodies that attack red blood cells. The results of an autoimmune reaction vary. Fever is common. Various tissues may be destroyed, such as blood vessels, cartilage, and skin. Virtually any organ can be attacked by the immune system, including the kidneys, lungs, heart, and brain. The resulting inflammation and tissue damage can cause kidney failure, breathing problems, abnormal heart function, pain, deformity, delirium, and death.

A large number of disorders almost certainly have an autoimmune cause, including lupus (systemic lupus erythematosus), myasthenia gravis, Graves' disease, Hashimoto's thyroiditis, pemphigus, rheumatoid arthritis, scleroderma, Sjögren's syndrome, pernicious anemia, multiple sclerosis and type I diabetes.

Immune diseases include but are not limited to conditions involving T-cells and/or macrophages such as acute and delayed hypersensitivity, graft rejection and graft-versus-host disease.

REFERENCE LIST

Carpino, L. A.; Giza, C. A.; Carpino, B. A. O-Acylhydroxylamines. I. Synthesis of O-Benzoylhydroxylamine. *J. Am. Chem. Soc.* 1959, 81, 955-957.

Fehrentz, J. A.; Castro, A. An Efficient Synthesis of Optically Active—(t-Butoxycarbonylamino)-aldehydes from—Amino Acids. *Synthesis* 2000, 8, 676-678.

Niedrich, H. *Chem. Ber.* 1969, 102, 1557-1569.

Shahak, I.; Almog, J. *Synthesis* 1969, 170-172.

Yasuma, T.; Oi, S.; Choh, N.; Nomura, T.; Furuyama, N.; Nishimura, A.; Fujisawa, Y.; Sohda, T. *J. Med. Chem.* 1998, 41, 4301-4308.

SUMMARY OF THE INVENTION

The invention relates to inhibitors of cysteine proteases having the general formulas I or II below:

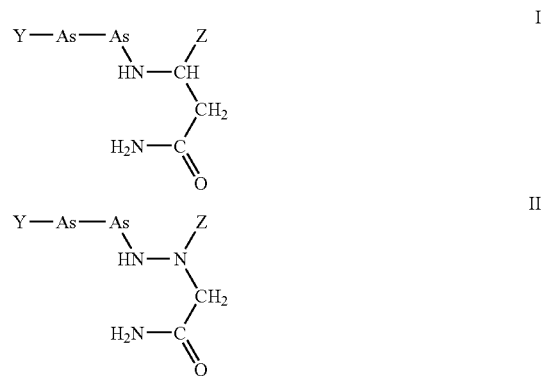

wherein:

As stands for any amino acid, or mimetics thereof and where Y stands for any acyl-residue including urethanes and peptides, preferably peptides having 2 to 10 amino acids, or any alkyl residue. Examples of amino acids which can be used in the present invention are L and D-amino acids, N-methyl-amino-acids; allo- and threo-forms of Ile and Thr, which can, e.g. be $\alpha$-, $\beta$- or $\omega$-amino acids, whereof $\alpha$-amino acids are preferred.

Examples of amino acids are:

aspartic acid (Asp), glutamic acid (Glu), arginine (Arg), lysine (Lys), histidine (His), glycine (Gly), serine (Ser) and cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-amino octanoic acid (Aoa), azetidine-(2)-carboxylic acid (Ace), pipecolic acid (Pip), 3-amino propionic, 4-amino butyric and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), Acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethyicysteine (AECys), carboxymethylcysteine (Cmc), dehydroalanine (Dha), dehydroamino-2-butyric acid (Dhb), carbbxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-Amino-4-cyanobutyric acid (Cba), cycloalkanecarboxylic aicds.

Examples of ω-amino acids are e.g.: 5-Ara (aminoraleric acid), 6-Ahx (aminohexanoic acid), 8-Aoc (aminooctanoic aicd), 9-Anc (aminovanoic aicd), 10-Adc (aminodecanoic acid), 11-Aun (aminoundecanoic acid), 12-Ado (aminododecanoic acid).

Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal), (2-Nal), 4-aminophenylalanin (Phe(4-$NH_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-$Cl_2$)), 3-fluorophenylalanine (Phe(3-F)), 4-fluorophenylalanine (Phe(4-F)), 3,4-fluorophenylalanine (Phe(3,4-$F_2$)), pentafluorophenylalanine (Phe($F_5$)), 4-guanidinophenylalanine (Phe(4-guanidino)), homophenylalanine (hPhe), 3-jodophenylalanine (Phe(3-J)), 4 jodophenylalanine (Phe(4-J)), 4-methylphenylalanine (Phe(4-Me)), 4-nitrophenylalanine (Phe-4-$NO_2$)), biphenylalanine (Bip), 4-phosphonomehtylphenylalanine (Pmp), cyclohexyglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-$J_2$)), d-methyl-tyrosine (Tyr(Me)), 3-$NO_2$-tyrosine(Tyr(3-$NO_2$)), phosphotyrosine (Tyr ($PO_3H_2$)), alkylglycine, 1-aminoindane-1-carboxy acid, 2-aminoindane-2-carboxy acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly($NH_2$)), diaminobutyric acid (Dab), 1,3-dihydro-2H-isoinole-carboxylic acid (Disc), homocylcohexylalanin (hCha), homophenylalanin (hPHe oder Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienyl)-alanine (Tha).

As can also stand for other amino acids than those encoded in the genetic code.

Proteinogenic amino acids are defined as natural protein-derived α-amino acids. Non-proteinogenic amino acids are defined as all other amino acids, which are not building blocks of common natural proteins.

Z stands for:
—CO—$CH_2$—W where W can be H, an optionally substituted alkyl, alkenyl, alkynyl, carbocyclic, aryl, heteroaryl, heterocyclic, $N_2$, halogen, O-alkyl, O-alkenyl, O-alkynyl, O-carbocyclic, O-aryl, O-heteroaryl, O-heterocyclic, O-acyl, S-alkyl, S-alkenyl, S-alkynyl, S-carbocyclic, S-aryl, S-heteroaryl, S-heterocyclic, S-acyl, C(O)-alkyl, C(O)-alkenyl, C(O)-alkynyl, C(O)-carbocyclic, C(O)-aryl, C(O)-heteroaryl, or C(O)-heterocyclic residue, or $N^+$(RR'R"), where R, R' and R" are independently from each other an optionally substituted acyl, alkyl, alkenyl, alkynyl, carbocyclic, aryl, heteroaryl, or heterocyclic residue, or —CO—NHO-Q where Q can be an optionally substituted acyl, alkenyl, alkynyl, aroyl, carbocyclic, heteroaryl, heterocyclic, aryl, or alkyl residue, or —$CR^1$=$CR^2$-EWG where $R^1$ and $R^2$ are independently from each other H, an optionally substituted alkyl, alkenyl, alkynyl, carbocyclic, heteroaryl, heterocyclic, or aryl residue, and are in cis or trans position to each other; and where EWG represents any electron-withdrawing group including
  $OR^4$, where $R^4$ can be H, an optionally substituted alkyl, alkenyl, alkynyl, carbocyclic, heteroaryl, heterocyclic or aryl residue,
  or C(O)O—$R^5$ where $R^5$ can be H, an optionally substituted alkyl, alkenyl, alkynyl, carbocyclic, heteroaryl, heterocyclic, acyl, aryl, or a substituted residue thereof,
  or $CH_2$O—$R^6$ where $R^6$ can be H, an optionally substituted alkyl, alkenyl, alkynyl, carbocyclic, heteroaryl, heterocyclic, acyl or aryl residue, or CN,
  or $SO_2R^7$ where $R^7$ can be H, an optionally substituted alkyl, alkenyl, alkynyl, carbocyclic, heteroaryl, heterocyclic, acyl or aryl residue,
  or $PO_2OR^8$ where $R^8$ can be H, an optionally substituted alkyl, alkenyl, alkynyl, carbocyclic, heteroaryl, heterocyclic, acyl or aryl residue.

Throughout the description and the claims the expression "acyl" can denote a $C_{1-20}$ acyl residue, preferably a $C_{1-8}$ acyl residue and especially preferred a $C_{1-4}$ acyl residue, "carbocyclic" or cycloalkyl can denote a $C_{3-12}$ carbocyclic residue, preferably a $C_4$, $C_5$ or $C_6$ carbocyclic residue. "Heteroaryl" is defined as an aryl residue, wherein 1 to 4, preferably 1, 2 or 3 ring atoms are replaced by heteroatoms like N, S or O. "Heterocyclic" is defined as a cycloalkyl residue, wherein 1, 2 or 3 ring atoms are replaced by heteroatoms like N, S or O. The expression "alkyl" can denote a $C_{1-50}$ alkyl group, preferably a $C_{6-30}$ alkyl group, especially a $C_{8-12}$ alkyl group; an alkyl group may also be a methyl, ethyl, propyl, isopropyl or butyl group. The expression "aryl" is defined as an aromatic residue, preferably substituted or optionally unsubstituted phenyl, benzyl, naphthyl, biphenyl or anthracene groups, which preferably have at least 8 C ring atoms; the expression "alkenyl" can denote a $C_{2-10}$ alkenyl group, preferably a $C_{2-6}$ alkenyl group, which has the double bond or the double bonds at any desired location and may be substituted or unsubstituted; the expression "alkynyl" can denote a $C_{2-10}$ alkynyl group, preferably a $C_{2-6}$ alkynyl group, which has the triple bond or the triple bonds at any desired location and may be substituted or unsubstituted; the expression "alkoxy" can denote a $C_{1-50}$ alkyl-oxygen group; the expression "alkenyloxy" can denote a $C_{2-10}$ alkenyl-oxygen group; the expression "alkynyloxy" can denote a $C_{2-10}$ alkynyl-oxygen group; the expression "carbocyclicoxy" can denote a $C_{3-12}$ carbocyclic-oxygen group; the expression "heteroaryloxy" can denote an aryl-oxygen group, wherein 1 to 4, preferably 1, 2 or 3 ring atoms are replaced by heteroatoms like N, S or O; the expression "heterocyclicoxy" can denote cycloalkyl-oxygen group, wherein 1, 2 or 3 ring atoms are replaced by heteroatoms like N, S or O; the expression "substituted" can denote any desired substitution by one or more, preferably one or two, alkyl, alkenyl, alkynyl, mono- or multi-valent acyl, alkoxy, alkoxyacyl, alkenyloxy, alkynyloxy, carbocyclicoxy, heteroaryloxy, heterocyclicoxy, alkoxyalkyl groups, any monoether or polyether containing identical or different alkyl, aryl, alkenyl, alkynyl, carbocyclic, heteroaryl, heterocyclic residues, or any monothioether or polythioether containing identical or different alkyl, aryl, alkenyl, alkynyl, carbocyclic, heteroaryl, heterocyclic residues; the afore-mentioned substituents may in turn have one or more (but preferably zero) alkyl, alkenyl, alkynyl, mono- or multi-valent acyl, alkoxyacyl or alkoxyalkyl groups as side groups which are preferably not substituted themselves. Organic amines, amides, alcohols or acids, each having from 8 to 50 C atoms, preferably from 10 to 20 C atoms, can have the formulae (alkyl)$_2$N— or alkyl-NH—, —CO—N(alkyl)$_2$ or —CO—NH(alkyl), -alkyl-OH or -alkyl-COOH.

The expression urethanes can denote a compound of the formula R'''NH—CO—OR'''', wherein R''' and R'''' are independently from each other optionally substituted alkyl, alkenyl, alkynyl, carbocyclic, heteroaryl, heterocyclic or aryl residues.

Peptide mimetics per se are known to a person skilled in the art. They are preferably defined as compounds which have a secondary structure like a peptide and optionally further structural characteristics; their mode of action is largely similar or identical to the mode of action of the native peptide; however, their activity (e.g. as an antagonist or inhibitor) can be modified as compared with the native peptide, especially vis à vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999.

The aim for using these mimetic structurs is increasing the activity, increasing the selectivity to decrease side effects, protect the compound (drug) against enzymatical degradation for prolongation of the effect.

Further peptide mimetics are defined in J. Gante, Angew. Chemie, 1994, 106, 1780-1802; V. J. Hruby et al., Biopolymers, 1997, 219-266; D. Nöteberg et al., 2000, 43, 1705-1713.

The present invention further includes within its scope prodrugs of the compounds of this invention. In general, such prodrugs will be functional derivatives of the compounds which are readily convertible in vivo into the desired therapeutically active compound. Thus, in these cases, the use of the present invention shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

These compounds are inhibitors of the cysteine protease legumain. These inhibitors may be used in pharmaceutical compositions. The pharmaceutical compositions, comprising one or more legumain inhibitors according to the present invention are useful for the treatment of legumain mediated diseases in a patient or subject.

DETAILED DESCRIPTION OF THE INVENTION

Biological Evaluation

The compounds were tested as inhibitors of legumain and checked for their cross-reactivity against two more cysteine proteases namely papain and cathepsin B. The activities are given in tables 1-3 for selected compounds of formulas 1-3.

No inhibition of papain and cathepsin B was observed at concentrations below 0.1 mM. The α,β-unsaturated compounds of the sulfone and phosphonates showed poor inhibition.

TABLE 1

Activities of the prepared compounds 5–13

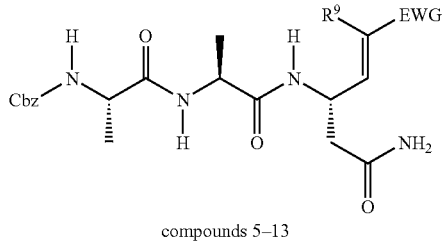

Formula 1 compounds 5–13

| Compd no. | R$^9$ | EWG | k$_{obs}$/[I] (M$^{-1}$s$^{-1}$) |
|---|---|---|---|
| 5 | H | CO$_2$CH$_3$ | 543 |
| 6 | H | CO$_2$CH$_2$CH$_3$ | 456 |
| 7 | H | CO$_2$CH$_2$CH=CH$_2$ | 776 |
| 8 | H | CO$_2$H | 4 |
| 9 | CH$_3$ | CO$_2$CH$_3$ | 2 |
| 10 | CH$_3$ | CO$_2$CH$_2$CH$_3$ | 2 |
| 11 | CH$_3$ | CO$_2$H | <1 |
| 12 | H | SO$_2$CH$_3$ | 30 |
| 13 | H | P(O)(OC$_2$H$_5$)$_2$ | <1 |

TABLE 2

Activity of the prepared compound 20

Formula 2

[Structure of compound 20: Cbz-Ala-Ala-Asn(CONH2)-NHO-benzoyl]

compound 20

| Compd no. | $K_i$ |
|---|---|
| 20 | $3.1 \pm 0.2 \times 10^{-6}$ M |

TABLE 3

Activities of the prepared compounds 18, 22 and 24

Formula 3

[Structure of compound 18, 22, 24]

compound 18, 22, 24

| Compd no. | Z | $k_{obs}/[I]$ (M$^{-1}$s$^{-1}$) |
|---|---|---|
| 18 | COCH$_2$Cl | 139088 |
| 22 | COCH$_2$Br | 84000 |
| 24 | COCH$_2$OC(O)C$_6$H$_5$ | 13 |

Synthesis

The inhibitors 5-13 were prepared as described in Scheme 1. The tripeptide was prepared starting from Z-Ala-Ala-OH (obtained from Bachem) via Z-Ala-Ala-OSu 1, followed by the coupling reaction with H-Asn(Trt)-OH (obtained from Bachem). The tripeptide-derivated Michael acceptors of the present invention were prepared generally as described in the following procedures. The tripeptide was converted into the aldehyde by reduction of the corresponding Weinreb amide with lithium aluminium hydride. The crude compound was transformed to the desired Michael acceptor compounds by the Wittig reaction with the corresponding phosphorane (Method A) or the Horner-Emmons reaction of the corresponding phophate ester with sodium bis(trimethylsilyl)amide or sodium hydride (Methods B, C). The trityl protecting group was removed by TFA in the presence of triisopropylsilane to give the inhibitors in good yields (Method D). The crude compounds were purified by preparative HPLC to give the desired inhibitors (Examples 1-9, compound 5-13).

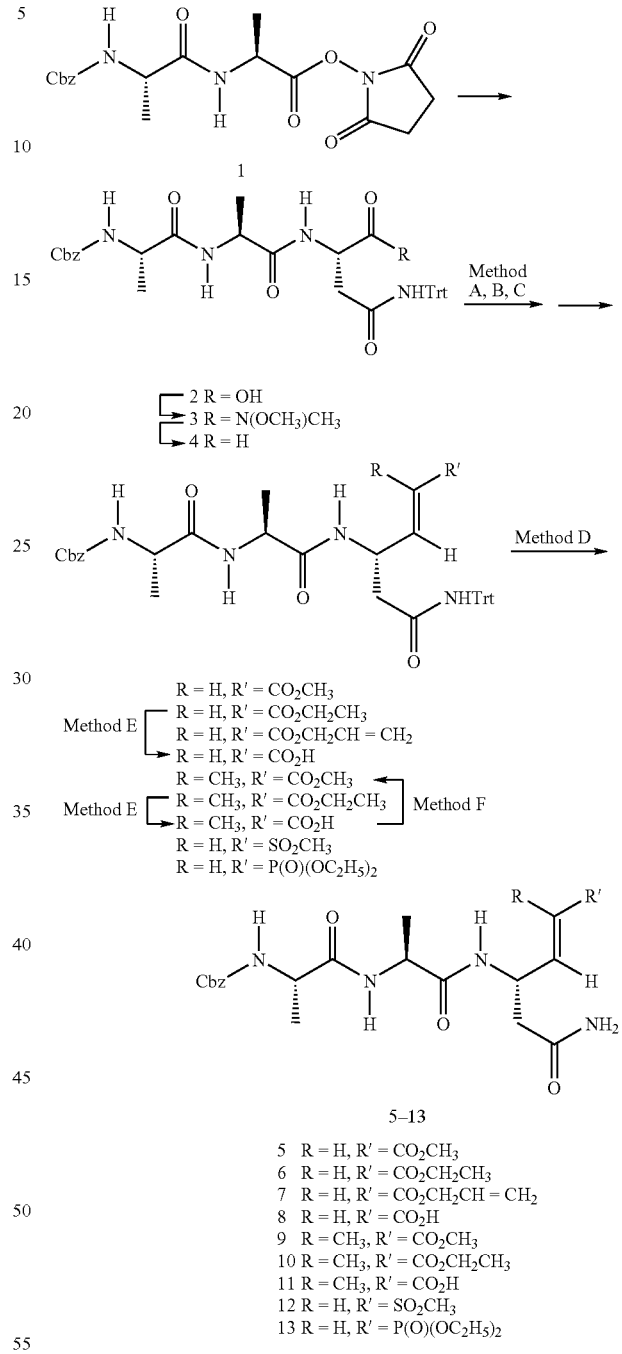

Scheme 1.
Synthesis of the compounds 5–13

The inhibitors 18, 22 and 24 were prepared as described in Scheme 2. The compound tert.-Butyl 2-(hydrazino)acetic acid was prepared from 80% hydrazine hydrate and t-butylbromoacetate according to the procedure of Niedrich, 1969. The hydrazine was coupled with Z-Ala-Ala-OSu 1 (prepared as described in Experimentals, Starting Material) to obtain the compound 14. Treatment of the t-butyl ester with TFA in dichloromethane provided the compound 15, which was converted into the compound 16 via coupling reaction with HATU, HOAt and triphenylmethylamine. Acylation with chloroacetyl chloride or bromoacetyl bromide gave the corresponding chloroacetyl and bromoacetyl derivative 17 and 21. The trityl protecting group was removed by TFA in the presence of triisopropylsilane to give the inhibitor 2-[2-(Cbz-L-Ala-L-Ala)-1-chloroacetyl)hydrazino]acetamide 18 and 22 (Method D). Treatment of 21 with benzoic acid in the presence of potassium fluoride was followed by treatment with trifluoroacetic acid (Method D) generated the benzoyloxymethylketone 24. The asparagine analogues were recognised by the protease resulting in potent inhibition. The second-order rate constant for the inactivation of legumain by the chloromethylketone (18), 139088 $M^{-1}s^{-1}$ is approximately 200 fold higher than that of the Michael acceptor inhibitors (Table 3). Whereas the bromomethylketone (22) is another potent inhibitor, the benzoyloxymethylketone (24) displays only moderate inhibition. Neither papain nor cathepsin B is inhibited by these inhibitors.

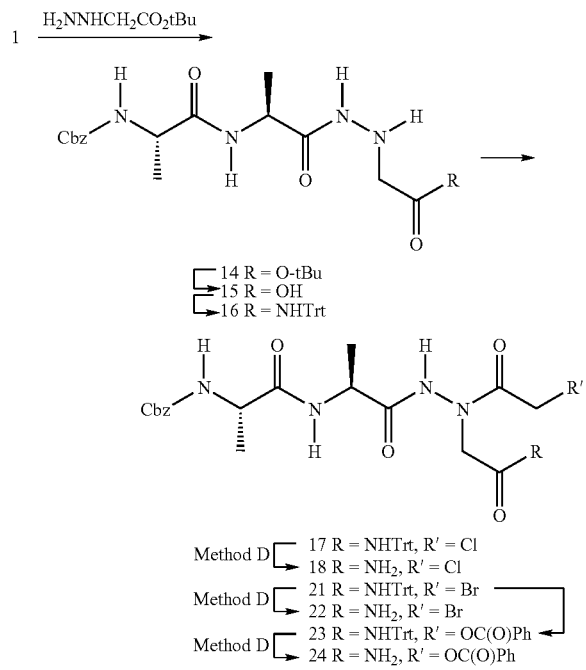

Furthermore we describe the preparation of another inhibitor 20 (Scheme 3) based on the N-peptidyl-O-acyl hydroxylamines Xaa-CO—NHO—CO—.

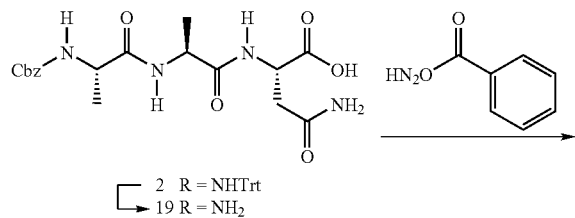

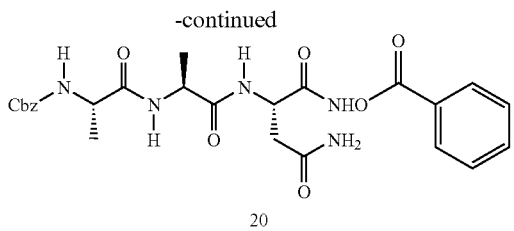

Experimental

NMR spectra were performed on Varian Unity 500, Varain Gemini 200 and Bruker AM 400 spectrometers. The following abbreviations are used: s, singlet; d, doublet; t, triplet; q, quartet; br., broad. Melting points were measured on a Leica Galen III melting point apparatus. ESI-MS: Mass spectra were taken with an MDS Sciex API 365 mass spectrometer equipped with an Ionspray™ interface (MDS Sciex; Thorn Hill, ON, Canada). The instrument settings, data acquisition and processing were controlled by the Applied Biosystems (Foster City, Calif., USA) Analyst™ software for Windows NT™. 50-100 scans were performed by the positive ionization Q1 scan mode to accumulate the peaks. Sample solutions were diluted with 50% methanol in 0.5% formic acid to reach concentrations about 10 μg/ml. Each sample solution was introduced directly by a microsyringe (1 ml) through an infusion pump (Havard Apperatus 22; Havard Instruments; Holliston, Mass., USA) and fused silica capillary tubing at a rate of 20 μl/min. Thin layer chromatography (TLC) was done with Macherey Nagel Polygram® SIL G/UV$_{245}$. Visualisation was accomplished by means of UV ligth at 254 nm, followed by dyeing with potassium permanganate or ninhydrin. Solvents were distilled prior to use. Petroleum ether with a boiling range of 35-65° C. was used. THF was distilled from sodium diphenyl ketyl immediately before use. All commercially available reagents were used without further purification. Reactions sensitive to air were carried out under an atmosphere of argon. The pH-7 buffer solution used in the workup procedures was prepared by dissolving potassium dihydrogen phosphate (85.0 g) and sodium hydroxide (14.5 g) in water (1 l). The compound dimethyl methylsulfonomethanephosphonate used for the preparation of inhibitor 8 was prepared according to the procedure of Shahak & Almog, 1969. For the purification a preparative HPLC [acetonitrile-water, gradient: 5-95%, flow rate: 6 ml min$^{-1}$, column: Nucleosil 7μ C18 100A, 250×21.2 mm (phenomenex), pump: L-6250 Merck-Hitachi] was used.

General Methods

Method A (Wittig Reaction): To a stirred solution of Z-Ala-Ala-Asn(Trt)-H (0.4 g, 0.63 mmol) in dry THF (10 ml) was added 1.1 equiv. of the corresponding phosphorane, obtained from Aldrich, Inc. The solution was stirred for four days. The solvent was removed under reduced pressure and the obtained residue was purified by flash chromatography to give the desired compounds.

Method B (Horner-Emmons Reaction, Base: Sodium bis(trimethylsilyl)amide): Sodium bis(trimethylsilyl)amide (1.84 ml, 0.756 mmol, prepared from hexamethyidisilazane (427 μl, 2.05 mmol) and sodium amide (80 mg, 2.05 mmol)) in absolute toluol (5 ml) was added to a solution of the corresponding phophate ester (1.2 equiv., 0.756 mmol, obtained from Aldrich, Inc.) in dry THF (4 ml) at 0° C. and stirred for 30 minutes at that temperature. A solution of Z-Ala-Ala-Asn(Trt)-H (0.4 g, 0.63 mmol) in dry THF (1 ml) was added. The mixture was stirred for 1.5 h, during which time it was allowed to warm to room temperature. After cooling with an ice-bath 0.5 N HCl (5 ml) was added and the organic material was extracted five times with ethyl acetate. The combined organic layers were dried over $Na_2SO_4$ and concentrated under reduced pressure. The compound was purified by flash chromatography.

Method C (Horner-Emmons Reaction, Base: Sodium Hydride): To a stirred suspension of sodium hydride (18.0 mg, 0.756 mmol, 95%, obtained from Aldrich, Inc.) in THF (4 ml) was added of the corresponding phophate ester (1.2 equiv., 0.756 mmol, obtained from Aldrich, Inc.) at 0° C. The mixture was stirred for 30 minutes at this temperature and a solution of Z-Ala-Ala-Asn(Trt)-H (0.40 g, 0.63 mmol) in dry THF (1 ml) was added. After stirring for 2.5 h at room temperature the mixture was cooled to 0° C. with an ice-bath and quenched with 0.5 N HCl (5 ml). The organic material was extracted five times with ethyl acetate. The combined organic layers were dried over $Na_2SO_4$ and concentrated under reduced pressure. The compound was purified by flash chromatography.

Method D (Deprotecting the Trityl Protecting): The trityl protecting group was removed as follows. Triisopropylsilane (277 µl, 1.35 mmol) and trifluoroacetic acid (7.5 ml) were added to a stirred solution of the protected compound (0.27 mmol) in $CH_2Cl_2$ (10 ml). This solution was stirred for 30 minutes at room temperature before it was diluted with toluol. The solvents were removed under reduced pressure and the obtained residue was triturated with $Et_2O$, and the resulted white solid was purified by preparative HPLC.

Method E (saponification): The isolated crude product (0.41 mmol) was dissolved in EtOH (3 ml) and 1 M NaOH was added (2.3 equiv. 0.943 mmol). After stirring for 3 h at room temperature the pH of the mixture was adjusted to 2-3 with 1N HCl. The organic material was extracted five times with ethyl acetate. The combined organic layers were dried over $Na_2SO_4$ and concentrated under reduced pressure.

Method F (esterification): The isolated crude compound (0.36 mmol) was dissolved in THF (5 ml) and a immediately before use prepared solution of diazomethane in ether was added until formation of gas ended. After 10 minutes 0.1 N HCl was added (5 ml) and the solvent was removed under reduced pressure. The organic material was extracted five times with ethyl acetate. The combined organic layers were dried over $Na_2SO_4$ and concentrated under reduced pressure.

Starting Material

Synthesis of Z-Ala-Ala-OSu (1)

The active ester Z-Ala-Ala-OSu (1) was prepared according to a procedure described in Bodansky, M., Bodansky, A., The Practice of Peptide Synthesis $2^{nd}$ Edition, Springer-Verlag. To a stirred solution of Z-Ala-Ala-OH (4.0 g, 13.6 mmol, obtained from Bachem) in 25 ml dry THF N-hydroxysuccinimide (1.56 g, 13.6 mmol) was added at 0° C. and the mixture was stirred for 10 minutes. A solution of dicyclohexylcarbodiimide (2.81 g, 13.6 mmol) in 3 ml dry THF was added. The mixture was stirred for 14 h, during which time it was allowed to warm to room temperature. The separated N,N'-dicyclohexylurea was removed by filtration and the solvent was evaporated in vacuo. The residue was twice recrystallized from isopropanol to give the active ester as a white solid (4.47 g, 84%) of m.p. 140° C.—TLC(MeOH/ $CHCl_3$, 1:50): $R_f$=0.5.—$^1$H NMR (400 MHz, DMSO-$d_6$): δ=1.20 (d, 3 H, J=7.0 Hz, $CH_3$), 1.44 (d, 3 H, J=7.4 Hz, $CH_3$), 2.79 (s, 4 H, 2×$CH_2$), 4.04-4.10 (m, 1 H, CH), 4.63-4.69 (m, 1 H, CH), 4.96-5.04 (m, 2 H, $CH_2$), 7.28-7.38 (m, 5 H, aryl-H), 7.45 (d, 1 H, J=7.8 Hz, NH), 8.58 (d, 1 H, J=7.0 Hz, NH).—MS (EI) m/z (%): 392 [M+H$^+$], 414 [M+Na$^+$], 430 [M+K$^+$].

Synthesis of Z-Ala-Ala-Asn(Trt)-OH (2)

The tripeptide Z-Ala-Ala-Asn(Trt)-OH (2) was prepared according to the following procedure: To a stirred solution of H-Asn(Trt)-OH (4.97 g, 13.28 mmol, obtained from Bachem) in dry DMF (25 ml) a solution of Z-Ala-Ala-OSu (5.2 g, 13.28 mmol) in dry DMF (20 ml) was added and stirred for 14 h at room temperature. The solvent was evaporated in vacuo by using an oil pump. The obtained crude compound was dissolved in ethyl acetate (100 ml), washed with 1 N HCl (2×30 ml) and water (30 ml). The organic layer was dried over $Na_2SO_4$, filtered and concentrated under reduced pressure to give the tripeptide as a white solid (7.95 g, 92%) of m.p. 196° C. The peptide was used without further purification.—$^1$H NMR (500 MHz, DMSO-$d_6$): δ=1.18 (d, 3 H, J=7.1 Hz, $CH_3$), 1.22 (d, 3 H, J=7.0 Hz, $CH_3$), 2.62-2.88 (m, 2 H, $CHCH_2$), 4.06-4.12 (m, 1 H, CH), 4.31-4.37 (m, 1 H, CH), 4.46-4.50 (m, 1 H, CH), 4.98-5.04 (m, 2 H, $CH_2O$), 7.15-7.35 (m, 20 H, aryl-H).—MS(EI) m/z (%): 651 [M+H$^+$], 673 [M+Na$^+$], 689 [M+K$^+$].

Synthesis of Z-Ala-Ala-Asn(Trt)-N(OCH$_3$)CH$_3$ (3)

The Weinreb amide Z-Ala-Ala-Asn(Trt)-N(OCH$_3$)CH$_3$ (3) was prepared according to the method of Yasuma, 1998: To a stirred solution of Z-Ala-Ala-Asn(Trt)-OH (0.5 g, 0.77 mmol), N,O-dimethylhydroxylamine hydrochloride (79 mg, 0.81 mmol), and triethylamine (114 µl, 0.82 mmol) in dry DMF (3 ml) were added diisopropylcarbodiimide (131 µl, 0.85 mmol) and HOBt (115 mg, 0.85 mmol) at 0° C., and the whole was stirred for 16 h during which time it was allowed to warm to room temperature. The mixture was concentrated under reduced pressure. The obtained crude compound was dissolved in $CH_2Cl_2$ (25 ml) and washed with aqueous citric acid, water, aqueous $NaHCO_3$, brine (5 ml per washing step). The organic layer was dried over $Na_2SO_4$, filtered and concentrated under reduced pressure to give the Weinreb amide as a white solid (0.49 g, 92%). The Weinreb amide was used without further purification.—TLC (MeOH/ $CHCl_3$, 1:30): $R_f$=0.49.—$^1$H NMR (400 MHz, CDCl$_3$): δ=1.26 (d, 3 H, J=7.0 Hz, $CH_3$), 1.29 (d, 3 H, J=7.0 Hz, $CH_3$), 2.64-2.76 (m, 2 H, $CHCH_2$), 2.86 (s, 3 H, $NCH_3$), 3.66 (s, 3 H, $OCH_3$), 3.76-3.83 (m, 1 H, CH), 4.07-4.13 (m, 1 H, CH), 4.33-4.40 (m, 1 H, CH), 5.02-5.09 (m, 2 H, $CH_2O$), 7.13-7.34 (m, 20 H, aryl-H).—MS (EI) m/z (%): 694 [M+H$^+$], 716 [M+Na$^+$], 732 [M+K$^+$].

Synthesis of Z-Ala-Ala-Asn(Trt)-H (4)

The aldehyde Z-Ala-Ala-Asn(Trt)-H (4) was prepared according to the method of Fehrentz and Castro, 2000: To a stirred solution of Z-Ala-Ala-Asn(Trt)-N(OCH$_3$)CH$_3$ (1.50 g, 2.16 mmol) in absolute THF (20 ml) was added dropwise lithium aluminium hydride (1.0 M, 2.7 ml, 2.7 mmol) at 0° C. After 15 minutes the mixture was hydrolyzed with aqueous citric acid (10 ml) and after brought to room temperature the solvent was evaporated in vacuo. The mixture was diluted with pH-7 buffer solution (15 ml). The organic material was extracted (5×30 ml) with ethyl acetate. The organic layer was dried over $Na_2SO_4$, filtered and concentrated under reduced pressure to give the aldehyde as a white solid (1.25 g, 91%), which was used without further purification.—TLC (MeOH/CHCl$_3$, 1:9): R$_f$=0.64.—$^1$H NMR (400 MHz, CDCl$_3$): δ=1.33 (d, 3 H, J=7.0 Hz, CH$_3$), 1.37 (d, 3 H, J=7.2 Hz, CH$_3$), 2.56-2.72 (m, 2 H, CHCH$_2$), 4.08-4.13 (m, 1 H, CH), 4.28-4.34 (m, 1 H, CH), 4.54-4.63 (m, 1 H, CH), 5.04-5.09 (m, 2 H, CH$_2$O), 7.24-7.32 (m, 20 H, aryl-H), 9.49 (s, 1 H, aldehyde).—MS (EI) m/z (%): 635 [M+H$^+$], 657 [M+Na$^+$], 732 [M+K$^+$].

Synthesis of tert.-Butyl 2-[2-(Cbz-L-Ala-L-Ala)-hydrazino]acetic acid (14)

Compound 14 was prepared as follows: To a stirred solution of Z-Ala-Ala-OSu (7.98 g, 20.4 mmol) in dry THF (50 ml) a solution of tert.-Butyl 2-(hydrazino)acetic acid (2.98 g, 20.4 mmol) in dry THF (20 ml) was added and stirred for 14 h at room temperature. The solvent was evaporated in vacuo. The obtained crude compound was triturated with water and filtered. The resulted solid was washed two times with a small amount of water, dried over P$_4$O$_{10}$ and used without further purification (5.6 g, 65%).—TLC (MeOH/CHCl$_3$, 1:9): R$_f$=0.53.—$^1$H NMR (400 MHz, CDCl$_3$): δ=1.35 (d, 3 H, J=7.0 Hz, CH$_3$), 1.36 (d, 3 H, J=7.1 Hz, CH$_3$), 1.44 (s, 9 H, t-Bu), 3.73 (s, br., 2 H, NHCH$_2$), 4.20-4.32 (m, 1 H, CH), 4.42-4.50 (m, 1 H, CH), 5.06-5.13 (m, 2 H, CH$_2$O), 5.39 (s, br., 1 H, NH), 5.58 (s, br., 1 H, NH), 7.02 (s, br., 1 H, NH), 7.28-7.38 (m, 5 H, aryl-H).—MS (EI) m/z (%): 423 [M+H$^+$], 445 [M+Na$^+$], 461 [M+K$^+$].

Synthesis of 2-[2-(Cbz-L-Ala-L-Ala)-hydrazino] acetic acid (15)

Compound 15 was prepared as follows: tert.-Butyl 2-[2-(Cbz-L-Ala-L-Ala)-hydrazino]acetic acid (2.5 g, 5.9 mmol) was dissolved in a mixture of trifluoroacetic acid (40 ml), CH$_2$Cl$_2$ (40 ml) and methyl phenyl sulphide (2 ml). This solution was stirred for 2 h at room temperature before it was diluted with toluol. The solvents were removed under reduced pressure and the obtained residue was triturated with Et$_2$O and filtered. The resulted solid was washed three times with Et$_2$O and dried to give the desired compound as a white solid (1.57 g, 73%), which was used without further purification.—TLC (MeOH/CHCl$_3$, 1:9): R$_f$=0.15.—$^1$H NMR (200 MHz, DMSO-d$_6$): δ=1.15 (d, 3 H, J=7.0 Hz, CH$_3$), 1.17 (d, 3 H, J=7.0 Hz, CH$_3$), 3.40 (s, 2 H, NHCH$_2$), 3.97-4.11 (m, 1 H, CH), 4.17-4.27 (m, 1 H, CH), 4.94-5.07 (m, 2 H, CH$_2$O), 7.26-7.39 (m, 5 H, aryl-H), 7.92 (d, 1 H, J=7.3 Hz, NH), 9.35 (s, br., 1 H, NH).—MS (EI) m/z (%): 367 [M+H$^+$], 389 [M+Na$^+$], 405 [M+K$^+$].

Synthesis of 2-[2-(Cbz-L-Ala-L-Ala)-hydrazino] triphenylmethylacetamide (16)

Compound 16 was prepared as follows: 2-[2-(Cbz-L-Ala-L-Ala)-hydrazino]acetic acid (0.30 g, 0.82 mmol) was dissolved in dry DMF (5 ml) and cooled to 0° C. with an ice-bath. To this stirred solution were added HATU (0.31 mg, 0.82 mmol), HOAt (0.11 mg, 0.82 mmol), triphenylmethylamine (0.32 g, 0.82 mmol) and N-ethyldiisopropylamine (0.28 ml, 1.64 mmol) and the whole mixture was stirred for 16 h during which time it was allowed to warm to room temperature. The solvent was evaporated in vacuo by using an oil pump. The obtained crude compound was dissolved in ethyl acetate (25 ml), washed with 1 N HCl, water, aqueous NaHCO$_3$, and brine (5 ml per washing step). The organic layer was dried over Na$_2$SO$_4$, filtered and concentrated under reduced pressure. The obtained residue was purified by flash chromatography to give the desired compound as a solid (40 mg, 8%).—TLC (MeOH/CHCl$_3$, 1:9): R$_f$=0.15.—$^1$H NMR (500 MHz, DMSO-d$_6$): δ=1.15 (d, 3 H, J=7.1 Hz, CH$_3$), 1.16 (d, 3 H, J=7.1 Hz, CH$_3$), 3.42 (s, 2 H, NHCH$_2$), 4.02-4.08 (m, 1 H, CH), 4.19-4.25 (m, 1 H, CH), 4.96-5.03 (m, 2 H, CH$_2$O), 7.17-7.42 (m, 20 H, aryl-H), 7.96 (d, 1 H, J=7.3 Hz, NH), 9.68 (s, br., 1 H, NH).—MS (EI) m/z (%): 608 [M+H$^+$], 630 [M+Na$^+$], 646 [M+K$^+$].

Synthesis of 2-[2-(Cbz-L-Ala-L-Ala)-1-(chloro-acetyl)hydrazino]triphenylmethylacetamide (17)

Compound 17 was prepared as follows: To a stirred solution of compound 16 (40 mg, 66 μmol) in dry THF (1.5 ml) at 0° C. was added triethylamine (14 μl, 100 μmol) and chloroacetyl chloride (5.3 μl, 66 μmol). After stirring the mixture for 15 minutes the solvent was removed under reduced pressure. The obtained crude compound was purified by flash chromatography to give the product as a white solid (37 mg, 82%).—TLC (MeOH/CHCl$_3$, 1:9): R$_f$=0.26.—MS (EI) m/z (%): 684 [M+H$^+$, $^{35}$Cl], 686 [M+H$^+$, $^{37}$Cl], 706 [M+Na$^+$, $^{35}$Cl], 708 [M+Na$^+$, $^{37}$Cl] 722 [M+K$^+$, $^{35}$Cl], 724 [M+K$^+$, $^{37}$Cl].

Synthesis of Z-Ala-Ala-Asn-OH (19)

The tripeptide Z-Ala-Ala-Asn-OH (19) was prepared according to the procedure of Method D and was purified by flash chromatography to give the product as a white solid in 88% yield.—TLC (MeOH/CHCl$_3$, 1:9): R$_f$=0.10.—$^1$H NMR (500 MHz, DMSO-d$_6$): δ=1.18 (d, 3 H, J=7.1 Hz, CH$_3$), 1.20 (d, 3 H, J=7.2 Hz, CH$_3$), 2.45-2.52 (m, 2 H, CHCH$_2$), 4.02-4.09 (m, $_1$ H, CH), 4.26-4.31 (m, 1 H, CH), 4.47-4.51 (m, 1 H, CH), 4.97-5.04 (m, 2 H, CH$_2$O), 6.87 (s, br., 1 H, NH), 7.30-7.37 (m, 5 H, aryl-H), 7.92 (d, 1 H, J=7.3 Hz, NH), 7.98 (d, 1 H, J=7.9 Hz, NH).—MS (EI) m/z (%): 409 [M+H$^+$], 431 [M+Na$^+$], 447 [M+K$^+$].

Synthesis of 2-[2-(Cbz-L-Ala-L-Ala)-1-(bro-moacetyl)hydrazino]triphenylmethylacetamide (21)

Compound 21 was prepared as follows: To a stirred solution of 16 (57 mg, 94 μmol, 1.0 equiv) in dry THF (3 ml) at 0° C. was added triethylamine (20.0 μl, 140 μmol, 1.5 equiv) and bromoacetyl bromide (8.2 μmol, 94 μmol, 1.0 equiv). After stirring the mixture for 15 min, the solvent was removed under reduced pressure. The obtained crude compound was purified by flash chromatography, generating the product (55 mg, 80%) as a white solid of m.p. 93-100° C.—TLC (MeOH/CHCl$_3$, 1:9): R$_f$=0.68.—$^1$H NMR (400 MHz, DMSO-d$_6$): δ=1.16 (d, 3 H, J=7.0 Hz, CH$_3$), 1.23 (d, 3 H, J=7.4 Hz, CH$_3$), 4.04-4.10 (m, 1 H, CH), 4.13-4.18 (m, 1 H, CH), 4.25 [s, 2 H, C(O)CH$_2$Br], 4.29 (s, 2 H, NHCH$_2$), 4.94-5.03 (m, 2 H, CH$_2$O), 7.15-7.34 (m, 20 H, aryl-H), 7.43 (d, 1 H, J=7.4 Hz, NH), 8.17 (d, 1 H, J=8.6 Hz, NH), 8.92 (s, 1 H, NH), 10.71 (s, br., 1 H, NH).—MS (EI) m/z (%): 728 [M+H$^+$, $^{79}$Br], 730 [M+H$^+$, $^{81}$Br], 750 [M+Na$^+$, $^{79}$Br], 752 [M+Na$^+$, $^{81}$Br], 766 [M+K$^+$, $^{79}$Br], 768 [M+K$^{30}$, $^{81}$Br].

Synthesis of 2-[2-(Cbz-L-Ala-L-Ala)-1-(benzoy-loxyacetyl)hydrazino]triphenylmethyl-acetamide (23)

Compound 23 was prepared as follows: Dry KF (15 mg, 257 μmol, 2.5 equiv) was added to a stirred solution of 21

(75 mg, 103 µmol, 1.0 equiv) in dry DMF (4 ml) at room temperature. After stirring the mixture for 3 min, benzoic acid was added (15 mg, 123 µmol, 1.2 equiv) and the whole mixture was stirred for 16 h. The solvent was evaporated under vacuum by using an oil pump. The obtained crude compound (80 mg, 100% crude yield) was used without further purification.—TLC (MeOH/CHCl$_3$, 1:9): R$_f$=0.44.—MS (EI) m/z (%): 770 [M+H$^+$], 792 [M+Na$^+$], 808 [M+K$^+$].

Pharmaceutical Compositions

Additionally, the present invention includes the use of such a compound for the preparation of a medicament for the treatment of a condition mediated by modulation of the legumain activity in a subject. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically active carrier.

To prepare the pharmaceutical compositions of this invention, one or more active compounds or salts thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1-30 mg/kg) and may be given at a dosage of from about 0.1-300 mg/kg/day (preferred 1-50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The method of treating conditions modulated by legumain described in the present invention may also be carried out using a pharmaceutical composition comprising any of the compounds as defined herein and a pharmaceutically acceptable carrier. The pharmaceutical composition may contain between about 0.01 mg and 500 mg, preferably about 5 to 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic, preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, olyhydroxyethylaspartamidephenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

The compounds or compositions of the present invention may be taken before a meal, while taking a meal or after a meal.

When taken before a meal, the compounds or compositions of the present invention can be taken 1 hour, preferably 30 or even 15 or 5 minutes before eating.

When taken while eating, the compounds or compositions of the present invention can be mixed into the meal or taken in a separate dosage form as described above.

When taken after a meal, the compounds and compositions of the present invention can be taken 5, 15, or 30 minutes or even 1 hour after finishing a meal.

EXAMPLES

Example 1

Synthesis of Methyl (S)-(E)-4-[Cbz-L-Ala-L-Ala] amino-6-amino-6-oxo-2-hexenoate (5)

This compound was prepared starting from the aldehyde using the Horner-Emmons reaction (Method B) with sodium bis(trimethylsilyl)amide and trimethyl phophonoacatate followed by deprotecting the trityl protecting (Method D). The crude compound was purified by preparative HPLC to give the product as a white solid (43%) of m.p. 242° C.—TLC (MeOH/CHCl$_3$, 1:9): R$_f$=0.34.—$^1$H NMR (400 MHz, DMSO-d$_6$): δ=1.20 (d, 3 H, J=7.1 Hz, CH$_3$), 1.22 (d, 3 H, J=7.1 Hz, CH$_3$), 2.38 (d, 2 H, J=6.8 Hz, CHCH$_2$), 3.64 (s, 3 H, OCH$_3$), 4.01-4.14 (m, 1 H, CH), 4.16-4.25 (m, 1 H, CH), 4.73-4.75 (m, 1 H, CH), 4.96-5.05 (m, 2 H, CH$_2$O), 5.80 (d, 1 H, J=15.8 Hz, COCH=CH), 6.82 (dd, 1 H, J=15.8 Hz, J=4.8 Hz, COCH=CH), 6.94 (s, br., 1 H, NH), 7.30-7.34 (m, 5 H, aryl-H), 7.46 (d, 1 H, J=7.2 Hz, NH), 8.01 (d, 1 H, J=7.4 Hz, NH), 8.08 (d, 1 H, J=8.0 Hz, NH).—$^{13}$C NMR (100 MHz, DMSO-$d_6$): δ=17.89, 18.12 ($CH_3$), 46.64, 48.26, 50.03 (CH), 51.34 ($OCH_3$), 65.37 ($CH_2C_6H_5$), 119.70 (COCH=CH), 127.79, 127.85, 128.41, 137.12 (aryl-C), 148.45 (COCH=CH), 155.91, 166.14, 171.31, 171.63, 172.46 (C=O).—MS (EI) m/z (%): 449 [M+H$^+$], 471 [M+Na$^+$], 487 [M+K$^+$].

Example 2

Synthesis of Ethyl (S)-(E)-4-[Cbz-L-Ala-L-Ala]amino-6-amino-6-oxo-2-hexenoate (6)

This compound was prepared starting from the aldehyde using the Horner-Emmons reaction (Method B) with sodium bis(trimethylsilyl)amide and triethyl phophonoacatate followed by deprotecting the trityl protecting (Method D). The crude compound was purified by preparative HPLC to give the product as a white solid (56%) of m.p. 194-196° C.—TLC (MeOH/CHCl$_3$, 1:9): $R_f$=0.38.—$^1$H NMR (400 MHz, CD$_3$OD): δ=1.25 (t, 3 H, J=7.1 Hz, CH$_3$), 1.35 (d, 3 H, J=7.1 Hz, CH$_3$), 1.38 (d, 3 H, J=7.1 Hz, CH$_3$), 2.55 (d, 2 H, J=6.7 Hz, CHCH$_2$), 4.08-4.14 (m, 1 H, CH), 4.16 (q, 2 H, J=7.1 Hz, CH$_2$CH$_3$), 4.30-4.36 (m, 1 H, CH), 4.86-4.88 (m, 1H, CH), 5.06-5.12 (m, 2 H, CH$_2$O), 5.94 (d, 1 H, J=15.7 Hz, COCH=CH), 6.89 (dd, 1 H, J=15.7 Hz, J=5.1 Hz, COCH=CH), 7.27-7.37 (m, 5 H, aryl-H).—MS(EI) m/z (%): 463 [M+H$^+$], 485 [M+Na$^+$], 501 [M+K$^+$].

Example 3

Synthesis of Allyl (S)-(E)-4-[Cbz-L-Ala-L-Ala]amino-6-amino-6-oxo-2-hexenoate (7)

This compound was prepared starting from the aldehyde using the Wittig reaction (Method A) with allyl (triphenylphophoranylidene)acetate and deprotecting the trityl protecting (Method D). The crude compound was purified by preparative HPLC to give the product as a white solid (62%) of m.p. 182-184° C.—TLC (MeOH/CHCl$_3$, 1:9): $R_f$=0.41.—$^1$H NMR (400 MHz, DMSO-$d_6$): δ=1.21 (t, 3 H, J=7.0 Hz, CH$_3$), 1.22 (d, 3 H, J=7.0 Hz, CH$_3$), 2.55 (d, 2 H, J=6.8 Hz, CHCH$_2$), 4.01-4.06 (m, 1 H, CH), 4.20-4.26 (m, 1 H, CH), 4.59 (d, 2 H, J=5.3 Hz, CH$_2$CH=CH$_2$), 4.73-4.76 (m, 1H, CH), 4.98-5.05 (m, 2 H, CH$_2$O), 5.19-5.32 (m, 2 H, CH$_2$CH=CH$_2$), 5.82 (d, 1 H, J=15.7 Hz, COCH=CH), 5.88-5.97 (m, 1 H, CH$_2$CH=CH$_2$), 6.86 (dd, 1 H, J=15.7 Hz, J=4.7 Hz, COCH=CH), 6.95 (s, br., 1 H, NH), 7.30-7.42 (m, 5 H, aryl-H), 7.46 (d, 1 H, J=7.4 Hz, NH), 8.01 (d, 1 H, J=7.2 Hz, NH), 8.09 (d, 1 H, J=8.2 Hz, NH).—MS (EI) m/z (%): 475 [M+H$^+$], 492 [M+NH$_4^+$], 497 [M+Na$^+$], 513 [M+K$^+$].

Example 4

Synthesis of (S)-(E)-4-[Cbz-L-Ala-L-Ala]amino-6-amino-6-oxo-2-hexenoic acid (8)

This compound was prepared starting from the aldehyde using the Horner-Emmons reaction (Method B) with sodium bis(trimethylsilyl)amide and triethyl phophonoacatate. The saponification was carried out as described in Method E. The trityl protecting group was removed by TFA in the presence of triisopropylsilane (Method D). The crude compound was purified by preparative HPLC to give the product as a white solid (37%) of m.p. 205-208° C.—TLC (MeOH/CHCl$_3$, 1:9): $R_f$=0.19.—$^1$H NMR (400 MHz, CD$_3$OD): δ=1.34 (t, 3 H, J=6.8 Hz, CH$_3$), 1.37 (d, 3 H, J=6.8 Hz, CH$_3$), 2.55 (d, 2 H, J=6.8 Hz, CHCH$_2$), 4.10-4.14 (m, 1 H, CH), 4.31-4.36 (m, 1 H, CH), 4.84-4.88 (m, 1 H, CH), 5.04-5.11 (m, 2 H, CH$_2$O), 5.92 (d, 1 H, J=15.7 Hz, COCH=CH), 6.88 (dd, 1 H, J=15.7 Hz, J=5.1 Hz, COCH=CH), 7.28-7.35 (m, 5 H, aryl-H).—MS (EI) m/z (%): 435 [M+H$^+$], 457 [M+Na$^+$], 473 [M+K$^+$].

Example 5

Synthesis of Methyl (S)-(E)-4-[Cbz-L-Ala-L-Ala]amino-6-amino-2-methyl-6-oxo-2-hexenoate (9)

This compound was prepared starting from the aldehyde using Wittig reaction (Method A) with (carbethoxyethylidene)triphenylphophorane. The saponification was carried out as described in Method E and the carbonic acid was esterificated as described in Method F. The trityl protecting group was removed by TFA in the presence of triisopropylsilane (Method D). The crude compound was purified by preparative HPLC to give the product as a white solid (65%) of m.p. 188-191° C.—TLC (MeOH/CHCl$_3$, 1:9): $R_f$=0.54.—$^1$H NMR (400 MHz, CD$_3$OD): δ=1.33 (t, 3 H, J=7.1 Hz, CH$_3$), 1.34 (d, 3 H, J=7.1 Hz, CH$_3$), 1.91 (d, 3 H, J=1.4 Hz, COCCH$_3$=CH) 2.43-2.57 (m, 2 H, CHCH$_2$), 4.06-4.10 (m, 1 H, CH), 4.27-4.29 (m, 1 H, CH), 5.01-5.06 (m, 1 H, CH), 5.07-5.15 (m, 2 H, CH$_2$O), 6.61 (dd, 1 H, J=9.0 Hz, J=1.4 Hz, COCCH$_3$=CH), 7.29-7.38 (m, 5 H, aryl-H).—MS (EI) m/z (%): 463 [M+H$^+$], 485 [M+Na$^+$], 501 [M+K$^+$].

Example 6

Synthesis of Ethyl (S)-(E)-4-[Cbz-L-Ala-L-Ala]amino-6-amino-2-methyl-6-oxo-2-hexenoate (10)

This compound was prepared starting from the aldehyde using Wittig reaction (Method A) with (carbethoxyethylidene)triphenylphophorane. The isolated crude product was deprotected by TFA in the presence of triisopropylsilane (Method D). The crude compound was purified by preparative HPLC to give the product as a white solid (64%) of m.p. 200-204° C.—TLC (MeOH/CHCl$_3$, 1:9): $R_f$=0.33.—$^1$H NMR (400 MHz, DMSO-$d_6$): δ=1.15-1.21 (m, 9 H, 3×CH$_3$), 1.80 (d, 3 H, J=1.2Hz, COCCH$_3$=CH), 2.31-2.35 (m, 2 H, CHCH$_2$), 4.02-4.08 (m, 1 H, CH), 4.10 (q, 2 H, CH$_2$CH$_3$), 4.15-4.21 (m, 1 H, CH), 4.83-4.87 (m, 1 H, CH), 4.97-5.05 (m, 2 H, CH$_2$O), 6.46 (dd, 1 H, J=9.0 Hz, J=1.4 Hz, COCCH$_3$=CH), 6.86 (s, 1 H, NH), 7.30-7.35 (m, 5 H, aryl-H), 7.44 (d, 1 H, J=7.2 Hz, NH), 7.93 (d, 1 H, J=7.4 Hz, NH), 8.05 (d, 1 H, J=7.4 Hz, NH).—MS (EI) m/z (%): 477 [M+H$^+$], 499 [M+Na$^+$], 515 [M+K$^+$].

Example 7

Synthesis of (S)-(E)-4-[Cbz-L-Ala-L-Ala]amino-6-amino-2-methyl-6-oxo-2-hexenoic acid (11)

This compound was prepared starting from the aldehyde using Wittig reaction (Method A) with (carbethoxyethylidene)triphenylphophorane. The saponification was carried out as described in Method E. The trityl protecting group was removed by TFA in the presence of triisopropylsilane (Method D). The crude compound was purified by preparative HPLC to give the product as a white solid (32%) of m.p. 185-189° C.—TLC (MeOH/CHCl$_3$, 1:9): R$_f$=0.08.—$^1$H NMR (400 MHz, CD$_3$OD): δ=1.33 (t, 3 H, J=7.1 Hz, CH$_3$), 1.34 (d, 3 H, J=7.1 Hz, CH$_3$), 1.89 (d, 3 H, J=1.2 Hz, COCCH$_3$=CH), 2.42-2.58 (m, 2 H, CHCH$_2$), 4.07-4.10 (m, 1 H, CH), 4.28-4.31 (m, 1 H, CH), 5.00-5.06 (m, 1 H, CH), 5.12-5.16 (m, 2 H, CH$_2$O), 6.63 (dd, 1 H, J=9.0 Hz, J=1.2 Hz, COCCH$_3$=CH), 7.26-7.38 (m, 5 H, aryl-H).—MS (EI) m/z (%): 449 [M+H$^+$], 471 [M+Na$^+$], 487 [M+K$^+$].

Example 8

Synthesis of Methyl [(S)-(E)-3-[Cbz-L-Ala-L-Ala] amino-5-amino-5-oxo-1-petene]-sulfonate (12)

This compound was prepared starting from the aldehyde using the Horner-Emmons reaction (Method C) with sodium hydride and dimethyl methylsulfonomethanephosphonate[14] followed by deprotecting the trityl protecting (Method D). The crude compound was purified by preparative HPLC to give the product as a white solid (71%) of m.p. 193-195° C.—TLC (MeOH/CHCl$_3$, 1:9): R$_f$=0.13.—$^1$H NMR (400 MHz, CD$_3$OD): δ=1.34 (t,3H, J=7.2 Hz, CH$_3$), 1.38 (d, 3 H, J=7.2 Hz, CH$_3$), 2.58-2.61 (m, 2 H, CHCH$_2$), 2.92 (s, 3 H, SO$_2$CH$_3$), 4.09-4.16 (m, 1 H, CH), 4.24-4.34 (m, 1 H, CH), 5.04-5.17 (m, 3 H, CH, CH$_2$O), 6.68 (d, 1 H, J=15.2 Hz, COCH=CH), 6.85 (dd, 1 H, J=15.2 Hz, J=4.3 Hz, COCH=CH), 7.27-7.35 (m, 5 H, aryl-H).—MS (EI) m/z (%): 469 [M+H$^+$], 491 [M+Na$^+$], 507 [M+K$^+$].

Example 9

Synthesis of Diethyl [(S)-(E)-3-[Cbz-L-Ala-L-Ala] amino-5-amino-5-oxo-1-petenylphosphate (13)

This compound was prepared starting from the aldehyde using the Horner-Emmons reaction (Method C) with sodium hydride and tetraethyl methylendiphosphonate followed by deprotecting the trityl protecting (Method D). The crude compound was purified by preparative HPLC to give the product as a white solid (60%) of m.p. 95-97° C.—TLC (MeOH/CHCl$_3$, 1:9): R$_f$=0.32.—$^1$H NMR (400 MHz, CD$_3$OD): δ=1.26-1.38 (m, 12 H, 2×CH$_2$CH$_3$, 2×CHCH$_3$), 2.51-2.61 (m, 2 H, CHCH$_2$), 3.98-4.15 (m, 5 H, CH, 2×CH$_2$CH$_3$), 4.28-4.34 (m, 1 H, CH), 5.04-5.15 (m, 3 H, CH, CH$_2$O), 5.91 (dd, 1 H, J=35.4 Hz, J=17.4 Hz, COCH=CH), 6.85 (ddd, 1 H, J=21.9 Hz, J=17.6 Hz, J=4.5 Hz, COCH=CH), 7.28-7.37 (m, 5 H, aryl-H).—MS (EI) m/z (%): 527 [M+H$^+$], 549 [M+Na$^+$], 565 [M+K$^+$].

Example 10

Synthesis of 2-[2-(Cbz-L-Ala-L-Ala)-1-(chloroacetyl)hydrazino]acetamide (18)

The compound 18 was prepared starting from compound 17 (0.054 mmol) by deprotecting the trityl protecting (Method D). The crude compound was purified by preparative HPLC to give the product as a white solid (14 mg, 56%).—TLC (MeOH/CHCl$_3$, 1:9): R$_f$=0.20.—$^1$H NMR (500 MHz, DMSO-d$_6$): δ=1.18 (d, 3 H, J=6.8 Hz, CH$_3$), 1.23 (d, 3 H, J=6.8 Hz, CH$_3$), 4.02-4.08 (m, 1 H, CH), 4.15-4.23 (m, 1 H, CH), 4.40 (s, br., 2 H, NHCH$_2$), 4.96-5.03 (m, 2 H, CH$_2$O), 7.20 (s, 1 H, NH), 7.28-7.37 (m, 5 H, aryl-H), 7.47 (d, 1 H, J=7.3 Hz, NH), 8.22 (s, br., 1 H, NH), 10.58 (s, br, 1 H, NH).—MS (EI) m/z (%): 442 [M+H$^+$, $^{35}$Cl], 444 [M+H$^+$, $^{37}$Cl], 464 [M+Na$^+$, $^{35}$Cl], 466 [M+Na$^+$, $^{37}$Cl], 480 [M+K$^+$, $^{37}$Cl].

Example 11

Synthesis of [Cbz-L-Ala-L-Ala-L-Asn]-O-benzoylhydroxamate (20)

To a solution of O-Benzoylhydroxylamine hydrochloride (85 mg, 0.49 mmol, prepared as described in the procedure of Carpino et al., 1959) in water (5 ml) was added at room temperature a 1 M solution of sodium bicarbonate until the effervescence ended. The organic material was extracted three times with CH$_2$Cl$_2$ (10 ml per extraction). The combined organic layers were dried over Na$_2$SO$_4$ and concentrated under reduced pressure to give O-Benzoylhydroxylamine (49 mg, 73%). In a second flask Z-Ala-Ala-Asn-OH (19) (130 mg, 0.318 mmol) was dissolved in a mixture of dry THF (5 ml) and dry DMF (3 ml). To this stirred solution were added isobutyl chloroformate (41 μl, 0.318 mmol) and NMM (35 μl, 0.318 mmol) at −15° C. After stirring for 15 minutes O-Benzoylhydroxylamine in dry THF (2 ml) was added and the mixture was stirred 14 h, during which time it was allowed to warm to room temperature. The solvent was evaporated in vacuo and the obtained residue was washed with cold KHSO$_4$ (5% in water, 5 ml). The precipitate was dissolved in ethyl acetate (10 ml), washed with water (3×5 ml) and dried over Na$_2$SO$_4$. After filtration the solvent was evaporated under reduced pressure. The crude compound was purified by preparative HPLC to give the product as an oil (77 mg, 46%).—TLC (MeOH/CHCl$_3$, 1:9): R$_f$=0.31.—$^1$H NMR (500 MHz, DMSO-d$_6$): δ=1.19 (d, 3 H, J=6.9 Hz, CH$_3$), 1.21 (d, 3 H, J=7.0 Hz, CH$_3$), 2.78-2.96 (m, 2 H, CHCH$_2$), 4.04-4.08 (m, 1 H, CH), 4.25-4.34 (m, 1 H, CH), 4.48-4.55 (m, 1 H, CH), 4.97-5.04 (m, 2 H, CH$_2$O), 7.26-7.42 (m, 10 H, aryl-H), 7.93 (d, 2 H, J=8.2 Hz, NH).—MS (EI) m/z (%): 528 [M+H$^+$], 550 [M+Na$^+$], 566 [M+K$^+$].

Example 12

Synthesis of 2-[2-(Cbz-L-Ala-L-Ala)-1-(bromoacetyl)hydrazino]acetamide (22)

Compound 22 was prepared starting from 21 (55 mg, 76 μmol) by the cleavage of the trityl protecting group. The crude compound was purified by preparative HPLC, generating the product (20 mg, 54%) as a white solid.—TLC (MeOH/CHCl$_3$, 1:50): R$_f$=0.22.—$^1$H NMR (500 MHz, DMSO-d$_6$): δ=1.18 (d, 3 H, J=7.0 Hz, CH$_3$) 1.24 (d, 3 H, J=7.0 Hz, CH$_3$), 4.00-4.10 (m, 1 H, CH), 4.08-4.12 (m, 1 H, CH), 4.26 [s, br., 2 H, C(O)CH$_2$Br], 4.38 (s, br., 2 H, NHCH$_2$), 4.96-5.03 (m, 2 H, CH$_2$O), 7.16 (s, 1 H, NH), 7.29-7.37 (m, 5 H, aryl-H), 7.43 (d, 1 H, J=7.3 Hz, NH), 8.18 (d, J=7.3 Hz, 1 H, NH), 10.59 (s, br., 1 H, NH).—MS (EI) m/z (%): 486 [M+H$^+$, $^{79}$Br], 488 [M+H$^+$, $^{81}$Br], 508 [M+Na$^+$, $^{79}$Br], 510 [M+Na$^+$, $^{81}$Br], 524 [M+K$^+$, $^{79}$Br], 526 [M+K$^+$, $^{81}$Br].

Example 13

Synthesis of 2-[2-(Cbz-L-Ala-L-Ala)-1-(benzoyloxyacetyl)hydrazino]acetamide (24)

Compound 24 was prepared starting from 23 (80 mg, 103 μmol) by the cleavage of the trityl protecting group. The crude compound was purified by preparative HPLC, generating the product as a white solid (8.7 mg, 16%).—TLC (MeOH/CHCl$_3$, 1:19): R$_f$=0.24.—$^1$H NMR (400 MHz, DMSO-d6): δ=1.20 (d, 3 H, J=7.1 Hz, CH$_3$), 127 (d, 3 H, J=7.1 Hz, CH$_3$), 4.04-4.10 (m, 1 H, CH), 4.21-4.26 (m, 1 H, CH), 4.38 (s, br., 2 H, NHCH$_2$), 4.78 [s, br., 2 H, C(O)CH$_2$O], 4.95-5.03 (m, 2 H, CH$_2$O), 7.18 (s, 1 H, NH), 7.28-7.36 (m, 4 H, aryl-H), 7.43 (d, 1 H, J=7.6 Hz, NH), 7.50-7.56 (m, 3 H, aryl-H), 7.65-7.70 (m, 1 H, aryl-H), 7.97-7.99 (m, 2 H, aryl-H), 8.22 (s, br., 1 H, NH), 10.60 (s, br., 1 H, NH).—MS (EI) m/z (%): 528 [M+H$^+$], 545 [M+NH$_4^+$], 550 [M+Na$^+$], 566 [M+K$^+$].

Example 13

Biological Evaluation

Fluorogenic Assay:

The legumain activity was determined in a fluorogenic continuos rate assay using the substrate Z-Ala-Ala-Asn-AMC on a Kontron spectrofluorometer SFM25 (exitation 380; emission 460) equipped with a four cell changer and controlled by an IBM-compatible personal computer. The obtained data were analyzed with the software FLUCOL$^{(38)}$. The assay were done at 37° C. or 30° C., using a sodium citrate buffer (39.5 mM citric acid/121 mM Na$_2$HPO$_4$) containing 1 mM dithiothreitol and 1 mM EDTA. Additionally, 0.1% (w/v) Chaps or 0.015% (w/v) Brij 35 was added.

The inhibition progress curves were analyzed using non-linear curve fitting software Prism Graph Pad to compute the k$_{obs}$ values. Approximate second-order inactivation constants (k$_{obs}$/[I]) were calculated for all compounds.

Example 14

Determination of k$_i$-Values

100 µl inhibitor stock solution were mixed with 100 µl buffer (HEPES pH 7.6) and 50 µl substrate Z-Ala-Ala-Asn-AMC and preincubated at 30° C. Reaction was started by addition of 20 µl enzyme solution. Formation of the product AMC was measured on a Kontron spectrofluorometer SFM25 (exitation 380; emission 460) and slopes were calculated. Legumain activity was measured at final substrate concentrations of 0.05, 0.1, 0.2, and 0.4 mM and further 7 inhibitor concentrations covering the IC$_{50}$ concentration. Calculations were performed using the GraFit 4.0.13 (Erithacus) Software.

We claim:

1. Compounds according to the general formula I or a pharmaceutical acceptable salt thereof,

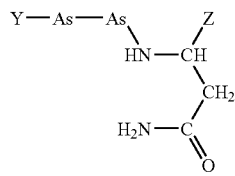

I wherein:
Y—As—As comprises Benzyl-oxy-carbonyl-Ala-Ala,
Z stands for:
—CO—CH$_2$—W where W can be H, an optionally substituted alkyl, alkenyl, alkynyl, carbocyclic aryl, heteroaryl, heterocyclic, N$_2$, halogen, O-alkyl, O-alkenyl, O-alkynyl, O-carbocyclic, O-aryl, O-heteroaryl, O-heterocyclic, O-acyl, S-alkyl, S-alkenyl, S-alkynyl, S-carbocyclic, S-aryl, S-heteroaryl, S-heterocyclic, S-acyl, C(O)-alkyl, C(O)-alkenyl, C(O)alkynyl, C(O)-carbocyclic, C(O)-aryl, C(O)-heteroaryl, or C(O) heterocyclic residue,
or —N$^+$(RR'R"), where R, R' and R" are independently from each other an optionally substituted acyl, alkyl, alkenyl, alkynyl, carbocyclic, aryl, heteroaryl, or heterocyclic residue,
or —CO—NHO-Q where Q is an optionally substituted acyl, alkenyl, alkynyl, aroyl, carbocyclic, heteroaryl, heterocyclic, aryl, or alkyl residue,
or —CR$^1$=CR$^2$-EWG where R$^1$ and R$^2$ are independently from each other H, an optionally substituted alkyl, alkenyl, alkynyl, carbocyclic, heteroaryl, heterocyclic, or aryl residue, and are in cis or trans position to each other; and where
EWG represents an electron-withdrawing group including OR$^4$, where R$^4$ can be H, an optionally substituted alkyl, alkenyl, alkynyl, carbocyclic, heteroaryl, heterocyclic or aryl residue,
or C(O)O—R$^5$ where R$^5$ can be H, an optionally substituted alkyl, alkenyl, alkynyl, carbocyclic, heteroaryl, heterocyclic, acyl, or aryl residue,
or CH$_2$O—R$^6$ where R$^6$ can be H, an optionally substituted alkyl, alkenyl, alkynyl, carbocyclic, heteroaryl, heterocyclic, acyl or aryl residue, or CN,
or SO$_2$R$^7$ where R$^7$ can be H, an optionally substituted alkyl, alkenyl, alkynyl, carbocyclic, heteroaryl, heterocyclic, acyl or aryl residue,
or PO$_2$OR$^8$ where R$^8$ can be H, an optionally substituted alkyl, alkenyl, alkynyl, carbocyclic, heteroaryl, heterocyclic, acyl or aryl residue, and pharmaceutically acceptable salts thereof.

2. A compound according to claim 1 wherein Z is —CO—NHO-Q and Q is an acyl group, preferably a benzoyl group.

3. A compound according to claim 1 wherein Z is —CR$^1$=CR$^2$ -EWG, R$^1$ and R$^2$ are each H and in trans-position to each other, and EWG is selected from the group consisting of —CO$_2$CH$_3$, —CO$_2$CH$_2$CH$_3$, —CO$_2$CH$_2$CH=CH$_2$, —CO$_2$H, —CO$_2$CH$_3$, —CO$_2$CH$_2$CH$_3$, —CO$_2$H, —SO$_2$CH$_3$, and —P(O)(OC$_2$H$_5$)$_2$.

4. A compound according to claim 1 wherein Z is —CO—CH$_2$—W and W is Cl or Br.

5. A composition comprising at least one compound of claim 1 and a carrier and/or diluent.

6. A process for making a composition comprising mixing at least one compound of claim 1 and a carrier and/or diluent.

7. Method for inhibiting legumain enzyme activity comprising contacting legumain with a compound of claim 1.

* * * * *